(12) United States Patent
Kolata et al.

(10) Patent No.: US 6,206,823 B1
(45) Date of Patent: Mar. 27, 2001

(54) SURGICAL INSTRUMENT AND METHOD FOR ENDOSCOPIC TISSUE DISSECTION

(75) Inventors: Ronald J. Kolata; Bennie Thompson, both of Cincinnati; Jason C. Bertin, Broadview Heights, all of OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/365,946

(22) Filed: Aug. 2, 1999

(51) Int. Cl.[7] .................................................. A61B 1/00
(52) U.S. Cl. ........................................ 600/129; 600/127
(58) Field of Search ..................................... 600/129, 127

(56) References Cited

U.S. PATENT DOCUMENTS

| | | | |
|---|---|---|---|
| Re. 36,043 | 1/1999 | Knighton | 600/101 |
| 3,224,320 | * 12/1965 | Knudsen | 600/129 |
| 3,297,022 | * 1/1967 | Wallace | 600/129 |
| 4,132,227 | * 1/1979 | Ibe | 600/129 |
| 5,271,380 | 12/1993 | Riek et al. | 128/4 |
| 5,334,150 | 8/1994 | Kaali | 604/164 |
| 5,373,840 | 12/1994 | Knighton | 128/4 |
| 5,376,076 | 12/1994 | Kaali | 604/164 |
| 5,380,291 | 1/1995 | Kaali | 604/164 |
| 5,385,572 | 1/1995 | Nobles et al. | 606/185 |
| 5,431,151 | 7/1995 | Riek et al. | 600/164 |
| 5,441,041 | 8/1995 | Sauer et al. | 600/106 |
| 5,448,990 | * 9/1995 | De Faria-Correa | 600/129 |
| 5,514,153 | 5/1996 | Bonutti | 606/190 |
| 5,551,947 | 9/1996 | Kaali | 604/264 |
| 5,569,291 | 10/1996 | Privitera et al. | 606/185 |
| 5,609,562 | 3/1997 | Kaali | 600/114 |
| 5,662,588 | 9/1997 | Iida | 600/121 |
| 5,667,480 | 9/1997 | Knight et al. | 600/210 |
| 5,685,820 | 11/1997 | Riek et al. | 600/114 |
| 5,700,236 | * 12/1997 | Sauer et al. | 600/129 |
| 5,720,761 | 2/1998 | Kaali | 606/185 |
| 5,722,934 | 3/1998 | Knight et al. | 600/201 |
| 5,725,479 | 3/1998 | Knight et al. | 600/210 |
| 5,836,945 | 11/1998 | Perkins | 606/41 |
| 5,902,315 | 5/1999 | Dubois | 606/190 |

* cited by examiner

Primary Examiner—Paul J. Hirsch
(74) Attorney, Agent, or Firm—Dean Garner

(57) ABSTRACT

A surgical instrument and method is provided for optically penetrating bodily tissue for creating an initial body cavity such as during a vessel harvesting procedure. The surgical instrument comprises an elongated shaft having a longitudinal axis, a proximal end, and a distal end. The surgical instrument further comprises an optical penetrating tip having a cylindrical portion attached to the distal end of the shaft, and a tapered portion extending distally therefrom. The tapered portion has an apex spaced laterally apart from the longitudinal axis. In one embodiment of the present invention, a handle is attached to the proximal end of the shaft.

11 Claims, 6 Drawing Sheets

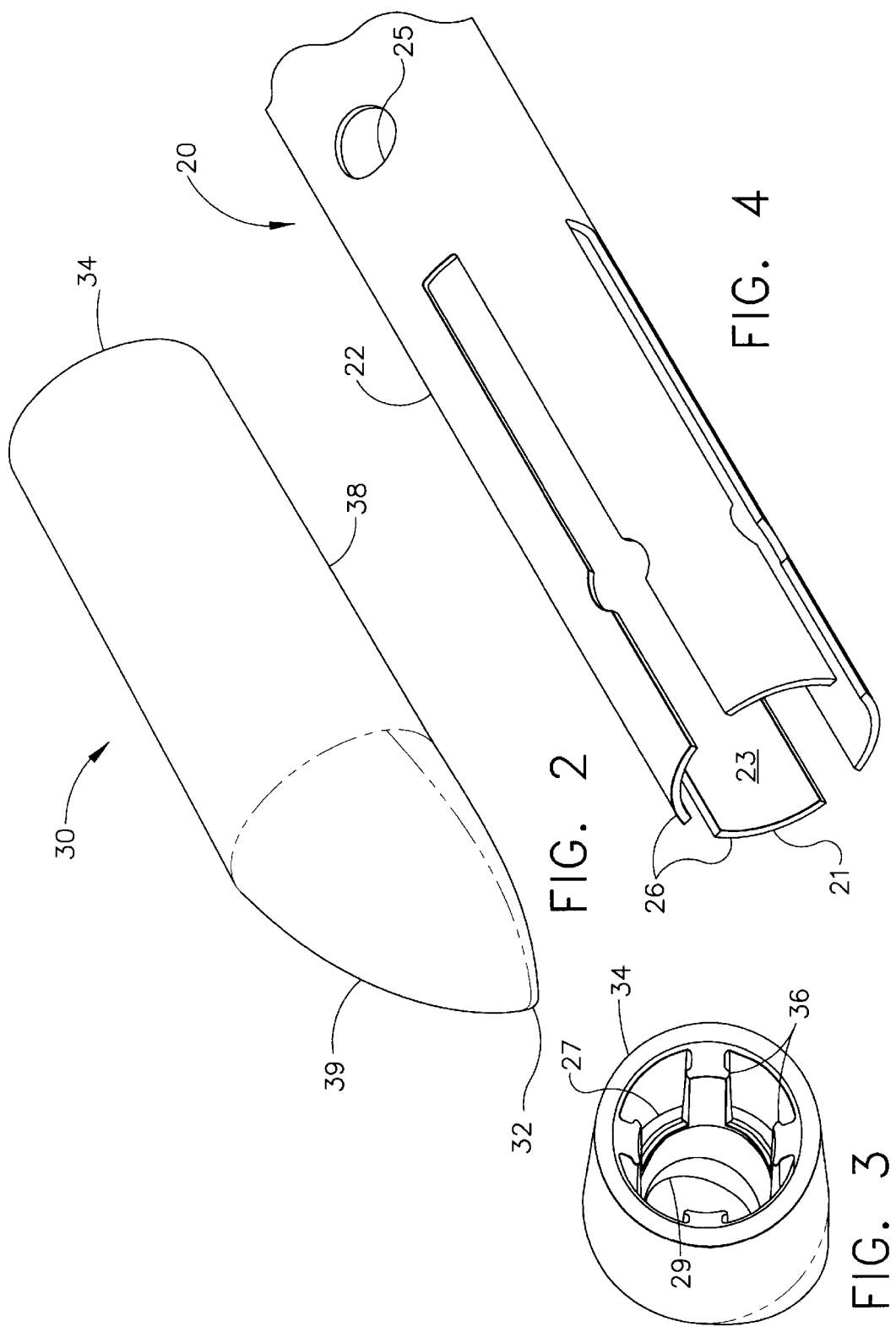

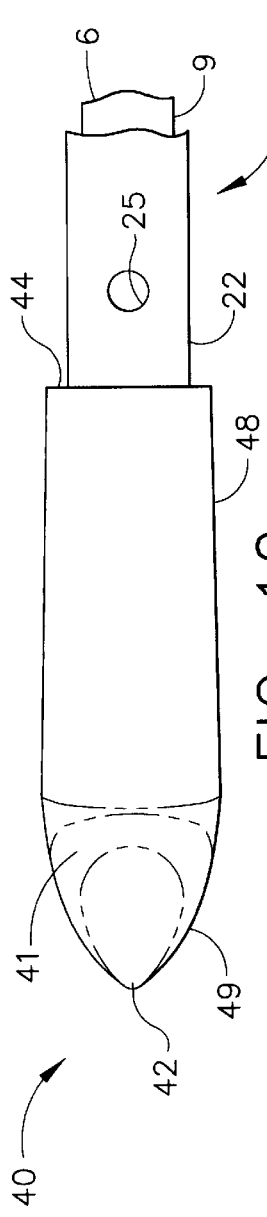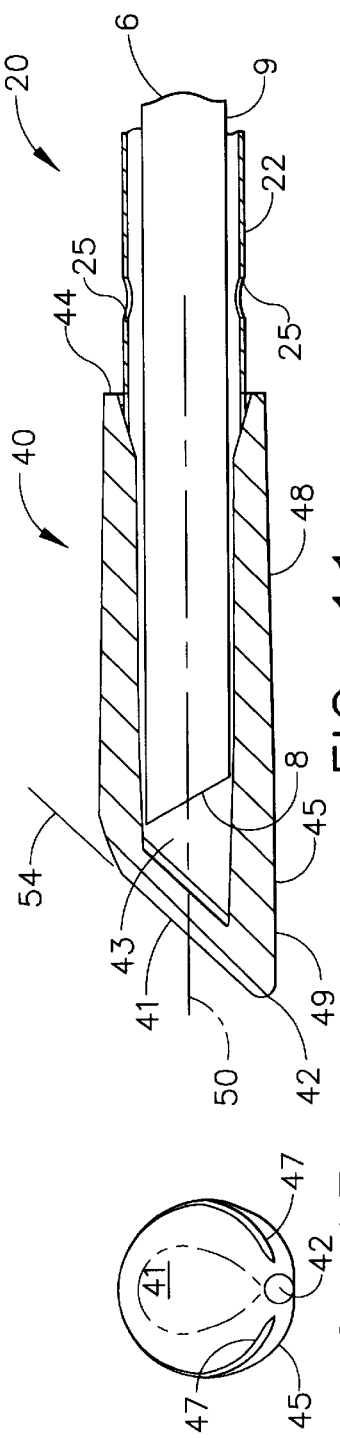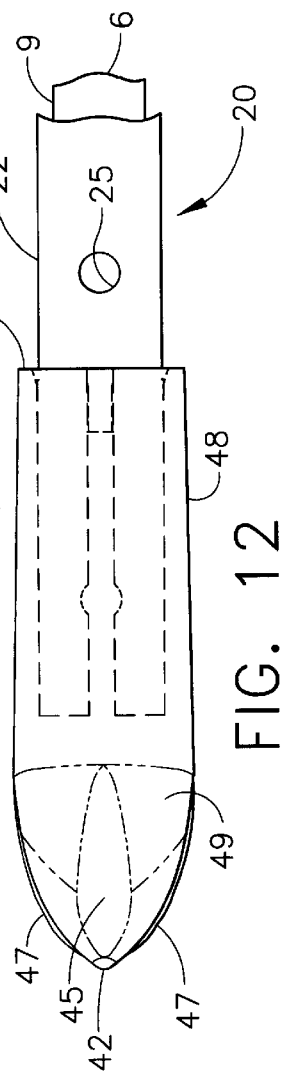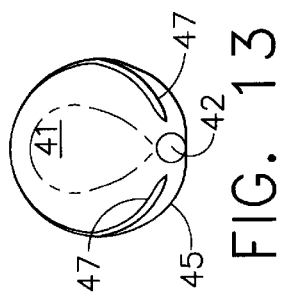
FIG. 10
FIG. 11
FIG. 12
FIG. 13

SURGICAL INSTRUMENT AND METHOD FOR ENDOSCOPIC TISSUE DISSECTION

This application is related to the following patent applications Ser. No. 08/919,548 filed on Aug. 28, 1997 now U.S. Pat. No. 5,922,004; Ser. No. 08/944,856 filed on Oct. 6, 1997 now U.S. Pat. No. 5,929,158; and Ser. No. 08/944,855 filed on Oct. 6, 1997 now U.S. Pat. No. 5,928,138.

FIELD OF THE INVENTION

The present invention relates, in general, to the dissection and retraction of bodily tissue and, more particularly, to new devices and endoscopic methods for harvesting a blood vessel to be used as a coronary artery bypass graft.

BACKGROUND OF THE INVENTION

Minimally invasive vessel harvesting has gained widespread acceptance in the field of surgery as a method for obtaining graft vessels for coronary artery bypass graft (CABG) procedures. When using such a method, for example, a long portion of the saphenous vein is removed from a patient's leg, operating through only one or a small number of short incisions in the leg. The vein is then segmented according to the number and type of grafts needed for the CABG procedure.

A surgical technique for the removal of a vessel such as a saphenous vein is disclosed in U.S. Pat. No. Re. 36, 043 issued to Knighton on Jan. 12, 1999 (hereinafter, Knighton). In this procedure, the surgeon uses an endoscope having a lumen through it. A grasping instrument is inserted in the lumen in order to grasp the saphenous vein, which is then withdrawn into the lumen of the endoscope. The endoscope is maneuvered along the length of the vein while side branches of the vein are ligated and transected whenever encountered. Although this surgical method provides for a minimally invasive technique, there are several drawbacks associated with it. First, in practicing this method, there is limited visibility of the saphenous vein and its side branches because viewing is limited to the immediate area directly in front of the endoscope. Second, the illumination within the subcutaneous space created by this type of endoscope is also limited to the light emitted directly at the distal portion of the endoscope. A third drawback to the described method is that the side branches of the saphenous vein limit the maneuverability of the endoscope. This limited maneuverability is because the outer edge of the endoscope body is prevented from advancing along the trunk of the saphenous vein until the encountered side branches are ligated and transected. Once free, the endoscope is then maneuvered until the next side branch is encountered. Moreover, it has been found that methods that use this type of endoscope (having a lumen) provide a restricted working space because the sidewalls of the endoscope body confine the working instrumentation to a limited area. A fourth drawback to the vessel harvesting method described in Knighton is that it requires a "three-handed" approach. One hand is required to hold and maintain the endoscope in position, a second hand is required to hold the free end of the transected vessel with a grasper, and a third hand (of an assistant) is required to dissect connective tissue away from the vessel.

Ethicon Endo-Surgery, Inc., Cincinnati, Ohio, has developed and promoted two very successful devices and an associated method for endoscopically harvesting blood vessels such as the saphenous vein. In this method, a surgeon (or surgical assistant) uses an optical tissue dissector known as the ENDOPATH SUBCU-DISSECTOR optical dissector for separating subcutaneous tissue away from the saphenous vein. Then the surgeon or assistant uses an optical retractor known as the ENDOPATH SUBCU-RETRACTOR optical retractor for retracting the dissected tissue away from the saphenous vein. Both of these devices have a transparent, concave working head having a spoon shape. The optical retractor has a larger, working head, however, than the optical dissector. The concave, working head defines a working space for the end effectors of an instrument such as a grasper, a scissors, or a clip applier. The optical dissector and optical retractor allow the surgeon to see the tissue on which is operated. These devices (hereinafter, Knight devices, Knight optical dissector, Knight optical retractor) and a surgical method for their use have been issued to Knight, et al, and are disclosed in U.S. Pat. No. 5,667,480 issued on Sep. 16, 1997 and in U.S. Pat. No. 5,722,934 issued on Mar. 3, 1998, both of which are hereby incorporated herein by reference.

The Knight optical dissector and retractor are each used with a thirty-degree endoscope in which the viewing angle of the distal end of the scope is slanted 30 degrees from the longitudinal axis of the instrument. The field of view is therefore directed ahead and to one side of the axis. This type of endoscope is ideal for use with the spoon shaped heads of the Knight devices because the surgeon desires to view the tissue directly ahead of the head and beneath the opening of the head where the tissue may be operated on.

In U.S. Pat. No. 5,902,315 issued to DuBois on May 11, 1999, and which is hereby incorporated herein for reference, a device (hereinafter, DuBois device) is described for dissecting and retracting a blood vessel from subcutaneous tissue. The DuBois device is similar to either of the Knight devices, and has the addition of a fluid carrying system for purging particulate matter from the working space of the concave head of either the optical dissector or optical retractor. A fluid flow (of carbon dioxide gas, for example) is used to purge smoke and/or mist from the enclosed working space in order to maintain visualization of the tissue being operated on. Particulate matter accumulates due to the use of electrosurgical or ultrasonic cutting devices, whereas condensation of moisture in the working space occurs due to the temperature differential between the inside and outside of the patient's body.

The Knight and DuBois devices and methods for their use for harvesting vessels represent a significant advance in the surgical art. Nevertheless, widespread use of these devices and methods has helped to clarify even more the needs of the surgeon for harvesting blood vessels. For example, for some surgeons or physician assistants, the repeated application of force required to advance the concave head of the Knight optical dissector in order to separate tissue from the vein can become physically tiring. This is especially true when harvesting a long (over 18 inches) portion of vein such as would be needed for a multiple CABG procedure. For these surgeons/assistants, the time required to dissect the vein can be several minutes longer than the time required by others who are better able to exert the manual dissection force required during the procedure. What is needed, therefore, is a device and method to reduce the initial dissection force required for separating the vein from surrounding tissue. Then the Knight or Dubois devices having the necessary concave heads for creating a working space could be inserted into the tissue more easily than before. Furthermore, the initial dissecting device and method should be used with the same, thirty-degree endoscope as is needed for the Knight devices to minimize the amount (and cost) of visualization equipment needed in the operating room.

In recent years, a number of penetrating optical instruments, sometimes referred to as optical trocars, have been developed for gaining access into a cavity in the surgical patient. One of the earliest examples is disclosed in U.S. Pat. No. 5,271,380 issued on Dec. 21, 1993 to Riek, et al. This penetration instrument has a hollow shaft for receiving an endoscope, and a transparent, conical distal end. Other examples of optical, penetration instruments are disclosed in the following U.S. Patents: U.S. Pat. No. 5,380,291 issued on Jan. 10, 1995 to Kaali; U.S. Pat. No. 5,441,041 issued on Aug. 15, 1995 to Sauer, et al; U.S. Pat. No. 5,423,848 issued on Jun. 13, 1995 to Washizuka. All of these patents describe instruments having transparent, conical tips, or the equivalent. In U.S. Pat. No. 5,569, 291 issued on Oct. 29, 1996 to Privitera, et al, a conical-tipped optical trocar is also disclosed. It is suggested that this surgical instrument may be used in "tunneling techniques to provide access to a desired surgical site remote from the point of entry" in connection with saphenous vein harvesting (see col. 4, line 43–44.)

In all of the references for optical, penetrating instruments cited in the present disclosure, the apex, or distal-most portion of the conical-shaped tip, lies on the central longitudinal axis of the instrument. These types of instruments are intended for use primarily with a zero-degree endoscope in which the field of view is directly ahead of the distal end of the endoscope. When the zero-degree endoscope is inserted into the optical, penetrating instrument, the apex is centered in the field of view, and it is possible to view images all around the apex within the field of view. If any of these conical-tipped instruments were to be used with a thirty-degree endoscope, the apex of the conical tip would be off-center of the field of view, and only images appearing on one side of the conical tip could be visualized. This would present a problem to the surgeon if such an arrangement were being used to "tunnel" along a blood vessel. Only one side or the other of the conical tip could be used as a window to see tissue. If the blood vessel being dissected from tissue happened to be on the "blind side" of the tip, then the surgeon, for example, may not be able to see side branches of the vessel as they are encountered. If side branches are "skipped" and not ligated and severed cleanly from the main trunk of the blood vessel, there would be significant danger of tearing side branches during the dissection of more distal portions of the blood vessel. It is clearly advantageous to be able to visualize all tissue adjacent to the optical penetrating tip. What is needed, therefore is an surgical instrument and method, which can be used as an initial dissection or "tunneling" instrument for vessel harvesting in combination with a thirty-degree endoscope. The surgical instrument, furthermore, should have an optical penetrating tip that allows visualization of all tissue adjacent to the optical penetrating tip.

SUMMARY OF THE INVENTION

The present invention is a surgical instrument for optically penetrating bodily tissue to create an initial body cavity. The surgical instrument comprises an elongated hollow shaft having a longitudinal axis, a proximal end, a distal end, and a lumen therethrough. The surgical instrument further comprises an optical penetrating tip having a cylindrical portion attached to the distal end of the hollow shaft and a tapered portion extending distally therefrom. The tapered portion has an apex spaced laterally apart from the longitudinal axis of the hollow shaft, thus allowing the surgeon to visualize all tissue adjacent to the tapered portion of the optical penetrating tip while being used in combination with an endoscope having a 30-degree tip.

In a preferred embodiment, a handle is attached to the proximal end of the hollow shaft for manipulating the surgical instrument through an incision of the surgical patient. The tapered portion of the optical penetrating tip has an upper surface blended into a lower surface, and the upper surface is sloped with respect to the longitudinal axis of the hollow shaft. The upper surface has an average inclination axis when viewed from the side and the average inclination axis forms an inclination angle with the longitudinal axis of the hollow shaft of between 15 and 75 degrees. A preferred inclination angle is about 45 degrees.

The surgical instrument further includes an endoscope for slidably insertion into the lumen of the hollow shaft. The endoscope has a conical field-of-view through the optical penetrating tip, whereby a central viewing axis of the field-of-view is directed thirty degrees from the longitudinal axis of the hollow shaft, and the apex of the optical penetrating tip is approximately in the center of the field-of-view of the endoscope.

The surgical instrument further includes at least one purge port in the distal end of the hollow shaft fluidly connected to a flow source, such as carbon dioxide gas. Particulate matter and moisture is purged from a body cavity created by the optical penetrating tip while the surgical instrument is inserted in the body cavity.

A method is provided for creating an initial body cavity alongside of a vessel to be harvested from a surgical patient's body comprising the steps of identifying a vessel to be removed, making an incision in the patient's body near the identified vessel, inserting a surgical instrument having an optical penetrating tip through the incision, optically penetrating the tissue along a side of the vessel with the optical penetrating instrument, and withdrawing the optical penetrating instrument from the body through the incision.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 2 is an isometric view of a first embodiment of an optical tip of the optical dissector shown in FIG. 1;

FIG. 3 is a partial, isometric view of a proximal end of the optical tip shown in FIG. 2;

FIG. 4 is an isometric view of a distal end of a shaft of the optical dissector shown in FIG. 1;

FIG. 10 is a top view of a second embodiment of an optical tip for the optical dissector shown in FIG. 1, and shown assembled on the shaft with an endoscope having a 30-degree tip inserted therein;

FIG. 11 is a side, sectional view of the optical tip, shaft, and endoscope shown in FIG. 10;

FIG. 12 is a bottom view of the optical tip, shaft, and endoscope shown in FIG. 10;

FIG. 13 is an end view of the optical tip shown in FIG. 10;

DETAILED DESCRIPTION OF THE INVENTION

Figure 1:
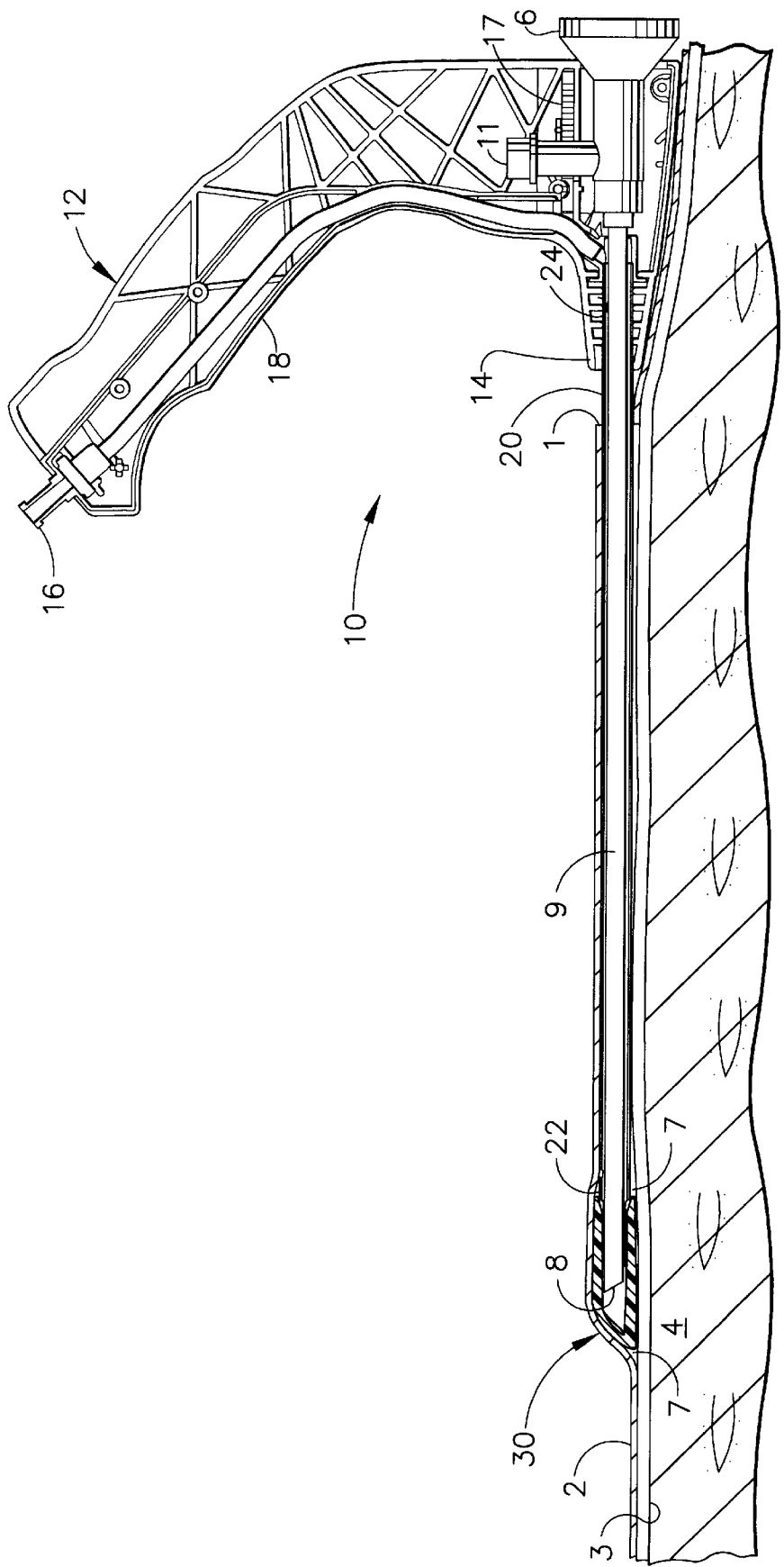
FIG. 1 is a sectional view of the present invention, an optical dissector (also referred to as a surgical instrument), as it is used in combination with an endoscope and is positioned between tissue layers of a surgical patient.

FIG. 1 is a side, sectional view of a first embodiment of the present invention, an optical dissector 10 (also referred to as a surgical instrument). Optical dissector 10 is positioned through incision 1 and between upper tissue layer 2 and lower tissue layer 4 of a surgical patient, and is shown being used in combination with an endoscope 6 having a 30-degree tip 8 to create an initial body cavity 7 alongside blood vessel 3. Optical dissector 10 comprises a hollow, elongated shaft 20 having a distal end 22 and a proximal end 24. Shaft 20 is preferably made of stainless steel tubing. In this embodiment, a plastic handle 12 for gripping and manipulating optical dissector 10 is attached to proximal end 24 of shaft 20. Handle 12 comprises an ergonomically shaped grip 18, a nose 14 for attachment to shaft 20, and a connector 16 for attaching optical dissector 10 to a flow source (not shown). Optical dissector 10 further comprises a hollow, transparent, optical tip 30 attached to distal end 22 of shaft 20. Endoscope 6 has an elongated, optical shaft 9 slidably inserted into shaft 20 so that a 30-degree tip 8 of endoscope 6 is positioned inside of optical tip 30 of optical dissector 10. An endoscope retaining guide 17 is provided in handle 12 for holding and aligning stem 11 of endoscope 6 in an upright position as shown, so that 30-degree tip 8 of endoscope 6 is oriented in a downward position as shown. As will be described for FIG. 15, this alignment of the endoscope 6 is advantageous for viewing tissues adjacent to optical tip 30.

FIG. 2 is an isometric view of optical tip 30, a first embodiment of the present invention and shown in FIG. 1. Optical tip 30 is asymmetrically shaped and comprises a tapered portion 39 having an apex 32. Optical tip 30 further comprises a cylindrical portion 38 and a proximal end 34. Optical tip 30 is optically transparent and has a uniformly thick wall in tapered portion 39. Optical tip 30 is preferably made of a rigid, medical grade, injection moldable plastic such as polycarbonate.

FIG. 3 is an isometric view of proximal end 34 of optical tip 30, showing a lumen 29 therein for attachment to distal end 22 of shaft 20 shown in FIG. 4. In this embodiment, four dovetail shaped ribs 36 are formed in proximal end 34 of optical tip 30 for attachment to four shaft flutes 26 formed into distal end 22 of shaft 20. This type of attachment is not intended to be detachable by the user. Other types of attachments are possible, including those types in which the user may detach optical tip 30 from shaft 20. This may be advantageous, for example, for surgical procedures requiring multiple versions of optical tip 30, each version having dissecting and/or optical characteristics specifically provided for particular steps of the surgical procedure. For all types of attachment, however, it is important that optical tip 30 not come off of shaft 20 while optical dissector 10 is positioned inside the body cavity of the patient.

FIG. 4 shows a lumen 23 extending through the entire length of shaft 20 for slidably inserting endoscope 6. FIG. 4 also shows a purge port 25 located proximal to where proximal end 34 of optical tip 30 would be positioned once assembled. At least one purge port 25 is provided and fluidly communicated to connector 16 of handle 12 as described for the DuBois device previously referenced in U.S. Pat. No. 5,902,315. Purge port 25 allows a flow of fluid, such as carbon dioxide gas, to be introduced into body cavity 7 of the patient during the surgical procedure. The fluid then escapes body cavity 7 along the outside of shaft 20 and out of incision 1 (see FIG. 1). This flow of fluid purges particulate matter including, for example, smoke and mist resulting from the use of electrosurgical or ultrasonic cutting instruments, which may be used in combination with optical dissector 10. This flow of fluid also helps to dry moisture forming on optical tip 30 due to condensation of water inside body cavity 7, thus improving the ability of the operator to view tissue adjacent to optical tip 30.

Figure 5:
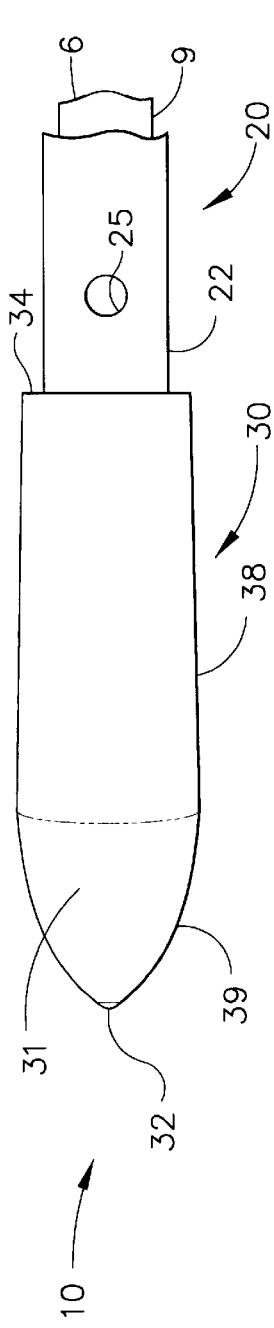
FIG. 5 is a top view of the optical tip shown in FIG. 2 and assembled on the shaft with an endoscope having a 30-degree tip inserted therein.
Figure 6:
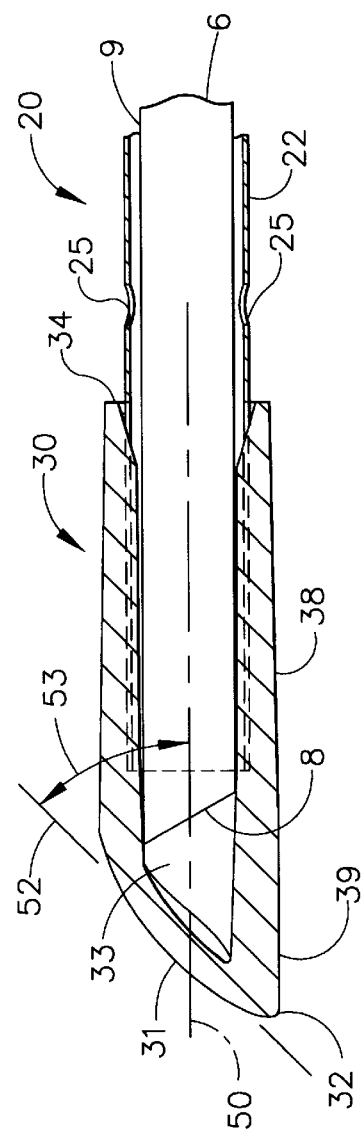
FIG. 6 is a side, sectional view of the optical tip, shaft, and endoscope shown in FIG. 5.
Figure 7:
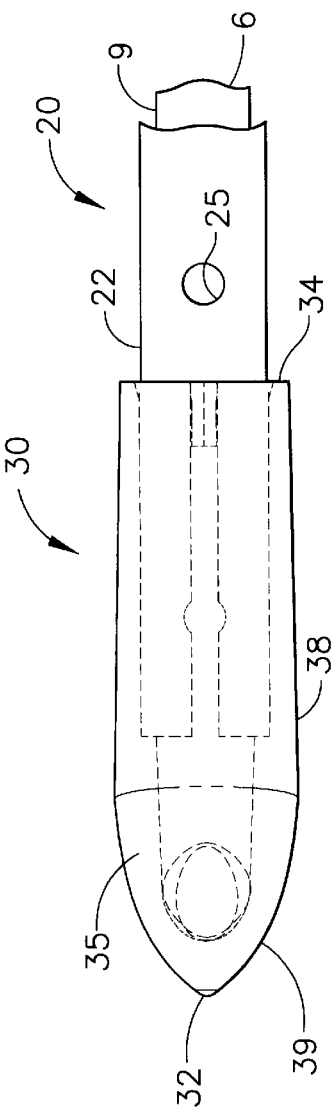
FIG. 7 is a bottom view of the optical tip, shaft, and endoscope shown in FIG. 5.
Figures 14, 15:
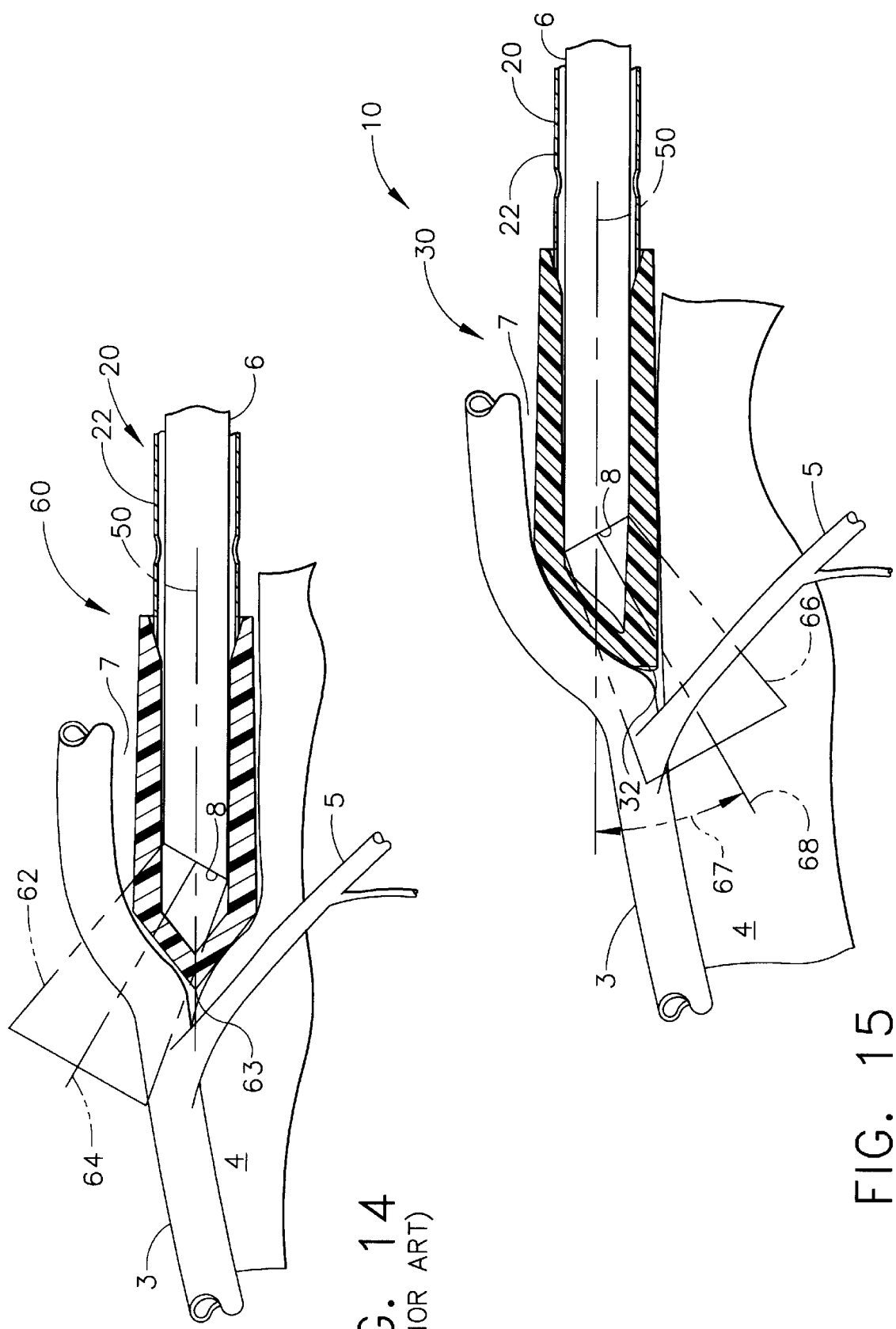
FIG. 14 is a side, sectional view of an optical dissector having a conical tip similar to a penetrating tip of a prior art instrument disclosed in U.S. Pat. No. 5,569,291, as it may be used with an endoscope having a 30-degree tip for harvesting a vessel.
FIG. 15 is a side, sectional view of the distal portion of the optical dissector shown in FIG. 1, wherein the optical dissector is used with an endoscope having a 30-degree tip for harvesting a vessel.

FIG. 5 is a top view, FIG. 6 is a side, sectional view, and FIG. 7 is a bottom view of optical dissector 30 shown in FIGS. 1 and 2, assembled onto distal end 22 of shaft 20. Optical shaft 9 of endoscope 6 is shown slidably inserted into shaft 20. A curved, upper surface 31 (see FIG. 5) of tapered portion 39 blends with a lower surface 35 (see FIG. 7). Upper surface 31 and lower surface 35 are rounded or non-planar, that is, neither has a flattened area. A 30-degree tip 8 of endoscope 6 is positioned within an optical tip chamber 33 and is oriented to view ahead and downwardly. The importance of this orientation of 30-degree tip 8 (also referred to as a distal viewing tip) is best understood by referring to FIGS. 14 and 15. FIG. 14 shows a conical tip 60 having a distal point 63 centered on a longitudinal axis 50. Conical tip 60 is shown assembled onto distal end 22 of shaft 20, and used in combination with endoscope 6 for separating blood vessel 3, having side branch 5, from lower tissue layer 4. Endoscope 6 has 30-degree tip 8, which has a field-of-view 62 centered on a viewing axis 64. The width of field-of-view 62 shown is not limited to what is illustrated in FIG. 14, and may be more or less depending on the optical characteristics of endoscope 6. Conical tip 60 is similar in shape to the optical trocar described in U.S. Patent 5,569,291, and is representative of the symmetrically shaped optical tips of the prior art. As is apparent in FIG. 14, side branch 5 and lower tissue layer 4 are not contained within the field-of-view 62 of endoscope 6. If endoscope 6 were rotated 180 degrees about axis 50 so that 30-degree tip 8 was pointed downwardly instead of upwardly, then blood vessel 3 would not be contained in field-of-view 62. In order to view blood vessel 3, side branch 5, and lower tissue layer 4 simultaneously when using conical tip 60, therefore, endoscope 6 must be provided with a zero-degree tip (not shown). A zero-degree tip views "straight-ahead" in the distal direction, and would allow point 63 to be approximately centered within field-of-view 62.

FIG. 15 shows the distal portion of optical dissector 10 of FIG. 6 used in combination with 30-degree tip 8 of endoscope 6 having an angled field-of-view 66 and an angled viewing axis 68. As FIG. 15 illustrates, apex 32 of optical tip 30 is approximately in the center of angled field-of-view 66 and closely aligned with an angled viewing axis 68. A viewing angle 67 is between angled viewing axis 68 and longitudinal axis 50. Blood vessel 3 and side branch 5 are also contained in angled field-of-view 66. The user may, therefore, advance optical dissector 10 while visualizing both blood vessel 3 and lower tissue layer 4 as they are separated. The user is also able to see side branch 5 as it is encountered.

Returning now to FIG. 6, the profile of upper surface 31 is shown to have an average inclination 52 with respect to longitudinal axis 50 of optical dissector 30. An inclination angle 53 between average inclination 52 and axis 50 is shown in the embodiment in FIG. 6 to be approximately 45 degrees. Inclination angle 53, however, may vary substantially. A smaller inclination angle 53 (a more tapered tip) advantageously reduces the force to "tunnel" into tissue. A larger inclination angle 53 (a blunter tip) advantageously decreases the distance between 30-degree tip 8 and the tissue being viewed. A compromise may be found, for example, in selecting inclination angle 53 to be approximately in the range of 15–75 degrees. What is important to maintain, no matter what the value for inclination angle 53, is that apex 32 is approximately centered in field of view 66 as shown in FIG. 15.

Figure 9:
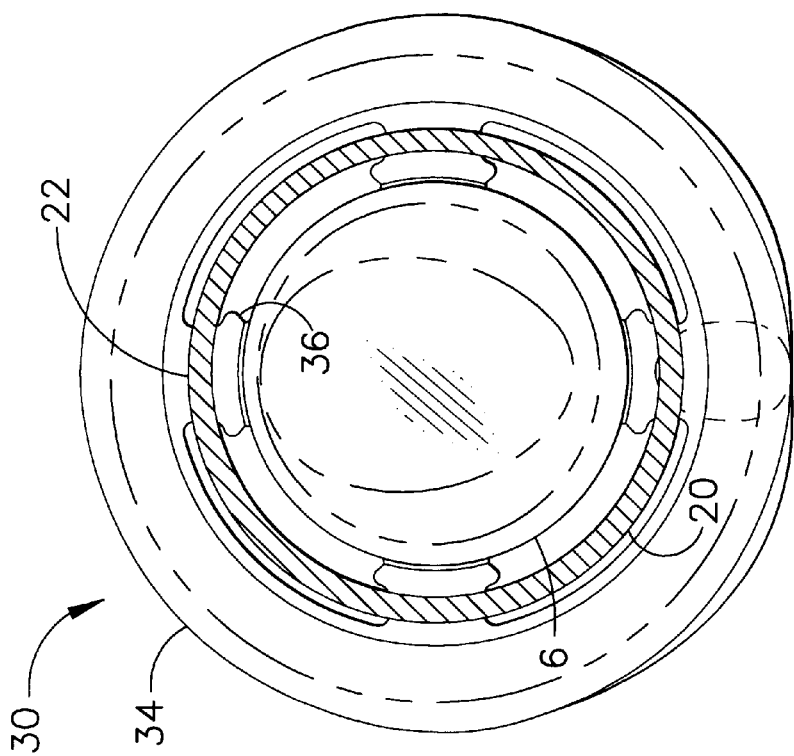
FIG. 9 is an enlarged, proximal end view of the optical tip shown in FIG. 5.
Figure 8:
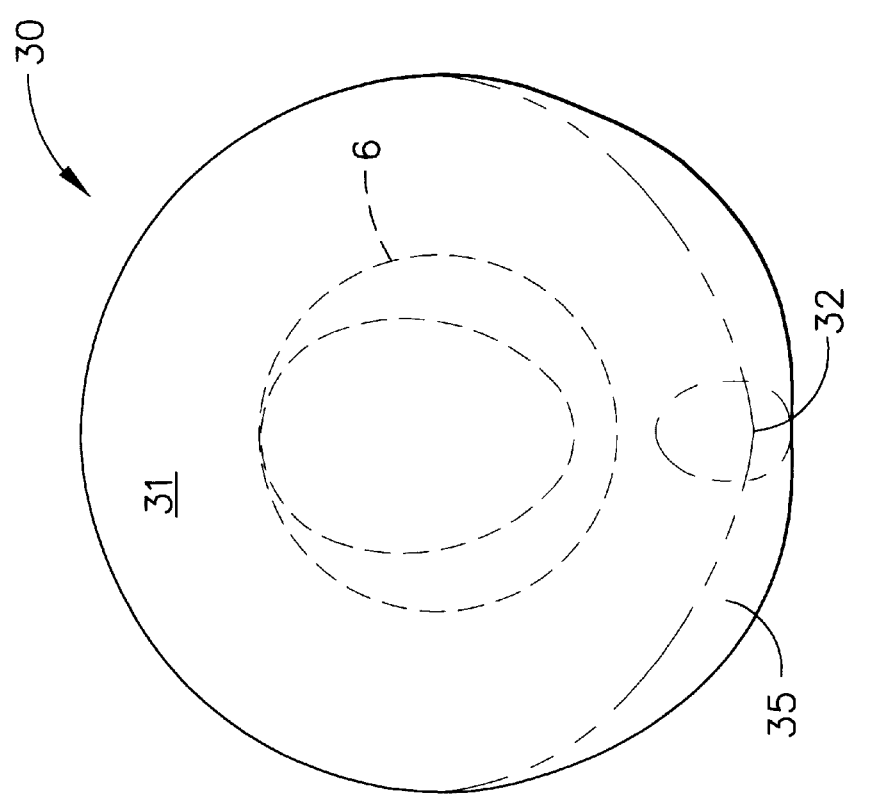
FIG. 8 is an enlarged, distal end view of the optical tip shown in FIG. 5.

FIGS. 8 and 9 are enlarged views of the distal and proximal ends, respectively, of the optical tip 30 shown in FIGS. 5, 6, and 7. FIG. 8 illustrates how upper surface 31 is blended into lower surface 35 in this embodiment. FIG. 9 shows how distal end 22 of shaft 20 is attached to ribs 36 of optical tip 30, providing radial clearance for the slidable insertion of endoscope 6.

FIGS. 10, 11, 12, and 13 are orthographic views of the distal portion of a second embodiment of the present invention. The second embodiment varies from the first embodiment shown in FIGS. 5, 6, and 7 in that an optical tip 40 of the second embodiment has a different shape than optical tip 30 of the first embodiment. Optical tip 40 comprises a cylindrical portion 48, a tapered portion 49, a proximal end 44 for attachment to shaft 20, and an apex 42 offset from longitudinal axis 50.

Optical tip 40 further comprises a flat, upper surface 41 blended with a lower surface 45. Endoscope 6 having 30-degree tip 8 (also referred to as a distal viewing tip) is shown slidably inserted into a optical tip chamber 43. Purge ports 25 are shown in shaft 20 proximal to optical tip 40. Optical tip 40 further comprises a pair of dissecting blades 47 molded onto or separately attached to tapered portion 49. Blades 47 are on opposite sides of tapered portion 49 and extend from apex 42 in approximately the proximal longitudinal direction. Blades 47 are provided to assist in separating tissue layers, but are not sharp enough to cut tissue.

Method of Use

The optical dissector 10, also referred to as an surgical instrument, of the present invention may be used in a wide variety of procedures requiring an initial penetration of tissue for creating a body cavity. One possible procedure is for harvesting a vessel, such as the saphenous vein, from a patient so that the vessel may be used later as a coronary artery bypass graft on that patient. The optical dissector 10 may be used for such a procedure in combination with the optical dissector/retractor having a transparent, concave head (also referred to as the DuBois device) disclosed in U.S. Pat. No. 5,902,315. A method for using optical dissector 10 to create body cavity 7 is described next while referring to FIGS. 1 and 15.

The surgeon first identifies blood vessel 3, such as the saphenous vein, to be harvested. A marker pen may be used to trace the underlying location of blood vessel 3 on the skin of the patient. The surgeon then makes an incision 1 in the tissue near blood vessel 3 using a cutting tool such as a scalpel. Next the surgeon places optical dissector 10 through incision 1 and maneuvers optical tip 30 over blood vessel 3, initially separating blood vessel 3 from upper tissue layer 2. As side branch 5 of blood vessel 3 is encountered, optical tip 30 is advanced carefully past side branch 5. Optical dissector 10 is advanced a short distance in the distal direction along blood vessel 3, and then retracted partially in the proximal direction, creating body cavity 7 alongside blood vessel 3. This is repeated a plurality of times and each time optical tip 30 is advanced a little farther in the distal direction until body cavity 7 is approximately equal to the length of blood vessel 3 to be harvested. Optical dissector 10 is then withdrawn through incision 1. The surgeon may then proceed with the vessel harvesting procedure using, for example, an optical retractor/dissector having a transparent concave head as disclosed in U.S. Pat. No. 5,902,315.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that only the spirit and scope of the appended claims limit the invention.

What is claimed is:

1. A surgical instrument for optically penetrating bodily tissue to create an initial body cavity and comprising:
   a. an elongated, hollow shaft having a longitudinal axis, a proximal end, and a distal end, said hollow shaft having a lumen therethrough; and
   b. a hollow and enclosed optical penetrating tip having a cylindrical portion attached to said distal end of said hollow shaft and a tapered portion extending distally therefrom, said tapered portion having an apex spaced laterally apart from said longitudinal axis.

2. The surgical instrument of claim 1 further comprising a handle attached to said proximal end of said hollow shaft.

3. The surgical instrument of claim 1 wherein said tapered portion of said optical penetrating tip comprises an upper surface blended into a lower surface, and said upper surface is sloped with respect to said longitudinal axis of said hollow shaft, and said upper surface has an average inclination axis when viewed from the side, and said average inclination axis forms an inclination angle with said longitudinal axis of said hollow shaft of between 15 and 75 degrees.

4. The surgical instrument of claim 2 wherein said tapered portion of said optical penetrating tip comprises an upper surface blended into a lower surface, and said upper surface is sloped with respect to said longitudinal axis of said hollow shaft, and said upper surface has an average inclination axis when viewed from the side, and said average inclination axis forms an inclination angle with said longitudinal axis of said hollow shaft of about 45 degrees.

5. The surgical instrument of claim 4 wherein said upper and lower surfaces of said tapered portion of said optical penetrating tip are non-planar.

6. The surgical instrument of claim 1 wherein said optical penetrating tip further comprises a hollow enclosed optical tip chamber in communication with said lumen of said hollow shaft for slidably inserting a distal viewing tip of an endoscope therein.

7. The surgical instrument of claim 1 wherein said optical penetrating tip is made from an optically transparent polymeric material and said tapered portion has a substantially uniform wall thickness.

8. The surgical instrument of claim 1 further comprising an endoscope slidably inserted into said lumen of said hollow shaft and positioned such that said endoscope has a tip having a field of view through said optical penetrating tip, said field of view having a central viewing axis therethrough, said central viewing axis making a viewing angle with respect to said longitudinal axis of at least about thirty degrees and said central viewing axis is closely aligned with said apex.

9. The surgical instrument of claim 1 further comprising at least one purge port in said distal end of said hollow shaft fluidly connected to a flow source, whereby particulate matter and moisture is purged from a body cavity created by said optical penetrating tip while said surgical instrument is inserted in said body cavity.

10. The surgical instrument of claim 9 wherein said flow source comprises carbon dioxide gas.

11. A method for creating an initial body cavity alongside of a vessel to be harvested from a surgical patient's body comprising the steps of identifying a vessel to be removed;

making an incision in the patient's body near the identified vessel;

inserting a surgical instrument having a hollow enclosed optical penetrating tip through said incision, said surgical instrument comprising an elongated, hollow shaft having a longitudinal axis, a proximal end, and a distal end, said optical penetrating tip having a cylindrical portion attached to said distal end of said hollow shaft and a tapered portion extending distally therefrom, said tapered portion having an apex spaced laterally apart from said longitudinal axis;

optically penetrating the tissue along a side of the vessel with the surgical instrument; and withdrawing the surgical instrument from the body through the incision.

* * * * *